US008951534B2

(12) United States Patent
Zurcher et al.

(10) Patent No.: US 8,951,534 B2
(45) Date of Patent: Feb. 10, 2015

(54) VACCINES FOR THE TREATMENT OF NEOPLASIAS FROM VIRAL CAPSIDS OF BIRNAVIRUS CONTAINING ANTIGENS OF THE HUMAN PAPILLOMAVIRUS

(75) Inventors: Thomas Zurcher, Tres Cantos (ES); Cayetano Von Kobbe, Tres Cantos (ES); Juan J. Bernal, Tres Cantos (ES); Ignacio Jiménez Torres, Tres Cantos (ES); Gloria Calderita Lucas, Tres Cantos (ES); Margarita Rodriguez Garcia, Tres Cantos (ES); Ana Garzon Gutierrez, Tres Cantos (ES); Virginia Gondar Sousa E Silva, Tres Cantos (ES); Arcadio García De Castro, Tres Cantos (ES); Irene Pino De La Huerga, Tres Cantos (ES)

(73) Assignee: Chimera Pharma, S.L.U, Tres Cantos (ES)

(*) Notice: Subject to any disclaimer, the term of this patent is extended or adjusted under 35 U.S.C. 154(b) by 14 days.

(21) Appl. No.: 13/504,875

(22) PCT Filed: Nov. 5, 2010

(86) PCT No.: PCT/ES2010/070717
§ 371 (c)(1),
(2), (4) Date: Jul. 11, 2012

(87) PCT Pub. No.: WO2011/054996
PCT Pub. Date: May 12, 2011

(65) Prior Publication Data

US 2012/0269844 A1 Oct. 25, 2012

(30) Foreign Application Priority Data

Nov. 6, 2009 (ES) .................................. 200930967

(51) Int. Cl.
*A61K 39/12* (2006.01)
*A61K 38/02* (2006.01)
*C12N 7/00* (2006.01)
*C07K 14/005* (2006.01)
*A61K 39/00* (2006.01)

(52) U.S. Cl.
CPC . *C12N 7/00* (2013.01); *A61K 39/12* (2013.01); *C07K 14/005* (2013.01); *A61K 2039/5258* (2013.01); *A61K 2039/585* (2013.01); *C07K 2319/00* (2013.01); *C12N 2710/20022* (2013.01); *C12N 2710/20023* (2013.01); *C12N 2710/20034* (2013.01); *C12N 2720/10022* (2013.01); *C12N 2720/10023* (2013.01)
USPC .................... 424/199.1; 424/202; 424/192.1; 435/69.7; 530/350

(58) Field of Classification Search
None
See application file for complete search history.

(56) References Cited

U.S. PATENT DOCUMENTS 7,476,387 B2 * 1/2009 Aguirre et al. ............ 424/192.1
2007/0015243 A1 * 1/2007 Aguirre et al. .............. 435/69.1
2007/0196339 A1 8/2007 Cid-Arregui et al.
2011/0190164 A1 8/2011 Zurcher et al.

FOREIGN PATENT DOCUMENTS

EP 2093281 A1 8/2009

OTHER PUBLICATIONS

Andreas M. Kaufmann et al. Vaccination trial with HPV16 L1E7 chimeric virus-like particles in women suffering from high grade cervical intraepithelial neoplasia (CIN 2/3). Int. J. Cancer: 121, 2794-2800 (2007).*
Torrens et al. Immunotherapy with CTL peptide and VSSP eradicated established human papillomavirus (HPV) type 16 E7-expressing tumors. Vaccine. Dec. 30, 2005;23(50):5768-74. Epub Aug. 8, 2005.*
Hallez S et al. Pre-clinical immunogenicity and anti-tumour efficacy of a deleted recombinant human papillomavirus type 16 E7 protein. Anticancer Res. Jul.-Aug. 2004;24(4):2265-75.*
GenBank: AAD30136.1 (disclosing SEQ ID No. 1), published on May 13, 1999.*
GenBank: AAD33253.1 (disclosing SEQ ID No. 2), published on Jun. 30, 2000.*
Tindle R W, et al., Chimeric Hepatitis B Core Antigen Particles Containing B- and TH-epitopes of Human Papillomavirus Type 16 E7 Protein Induce Specific Antibody and T-helper Responses in Immunised Mice, Virology, Academix Press, Orlando, US, vol. 200, No. 2, May 1, 1994.
Garriga Damia, et al., The 2.6-angstrom structure of infectious Bursal disease virus-derived T=1 particles reveals new stabilizing elements of the virus capsid, Journal of Virology, vol. 80, No. 14, Jul. 2006.
Remond M, et al., Infectious bursal disease subviral particles displaying the foot-and-mouth disease virus majo antigenic site, Vaccine, Elsevier Ltd, GB, vol. 27, No. 1, Jan. 1, 2009.
Winter Ursula et al, Progress in the development of a cervical cancer vaccine, Therapeutics and Clinical Risk Management Sep. 2006 LNKD-PUBMED: 18360601, vol. 2, No. 3, Sep. 2006.
Yousuf Sadaf et al., Prophylactic and therapeutic human papillomavirus vaccine, a breakthrough for women health, Pakistant Medical Association, Journal Pakistan Medical Association, Karachi, PK, vol. 59, No. 5, May 1, 2009.
International Search Report issued in PCT/ES2010/070717 on Jun. 17, 2011.
Coulibaly et al., Fasseli; "The Birnavirus Crystal Structure Reveals Structural Relationships Among Icosahedral Viruses"; Cell, vol. 120, 761-772; Mar. 25, 2005; 12 pgs.

* cited by examiner

*Primary Examiner* — Nicole Kinsey White
*Assistant Examiner* — Nick Zou
(74) *Attorney, Agent, or Firm* — Blank Rome LLP

(57) ABSTRACT

The invention relates to therapeutic vaccines for the treatment of neoplasias caused by the human papillomavirus (HPV). In particular, the vaccines of the present invention are formed by chimeric virus-like capsids of birnavirus containing papillomavirus antigens.

20 Claims, 2 Drawing Sheets

SEQUENCE LISTING

```
<160> NUMBER OF SEQ ID NOS: 21

<210> SEQ ID NO 1
<211> LENGTH: 512
<212> TYPE: PRT
<213> ORGANISM: Artificial Sequence
<220> FEATURE:
<223> OTHER INFORMATION: pVP2 of IBDV Soroa strain

<400> SEQUENCE: 1

Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160
```

```
Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Arg Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg Ile Ala Val Pro Val Val Ser Thr Leu Phe Pro
    450                 455                 460

Pro Ala Ala Pro Leu Ala His Ala Ile Gly Glu Gly Val Asp Tyr Leu
465                 470                 475                 480

Leu Gly Asp Glu Ala Gln Ala Ala Ser Gly Thr Ala Arg Ala Ala Ser
                485                 490                 495

Gly Lys Ala Arg Ala Ala Ser Gly Arg Ile Arg Gln Leu Thr Leu Ala
            500                 505                 510


<210> SEQ ID NO 2
<211> LENGTH: 98
<212> TYPE: PRT
<213> ORGANISM: Artificial Sequence
<220> FEATURE:
<223> OTHER INFORMATION: E7 of HPV-16

<400> SEQUENCE: 2

Met His Gly Asp Thr Pro Thr Leu His Glu Tyr Met Leu Asp Leu Gln
1               5                   10                  15
```

-continued

```
Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro


<210> SEQ ID NO 3
<211> LENGTH: 63
<212> TYPE: PRT
<213> ORGANISM: Artificial Sequence
<220> FEATURE:
<223> OTHER INFORMATION: E7 of HPV-16 wherein amino acids 1 to 35 have
      been eliminated

<400> SEQUENCE: 3

Asp Glu Ile Asp Gly Pro Ala Gly Gln Ala Glu Pro Asp Arg Ala His
1               5                   10                  15

Tyr Asn Ile Val Thr Phe Cys Cys Lys Cys Asp Ser Thr Leu Arg Leu
            20                  25                  30

Cys Val Gln Ser Thr His Val Asp Ile Arg Thr Leu Glu Asp Leu Leu
        35                  40                  45

Met Gly Thr Leu Gly Ile Val Cys Pro Ile Cys Ser Gln Lys Pro
    50                  55                  60


<210> SEQ ID NO 4
<211> LENGTH: 452
<212> TYPE: PRT
<213> ORGANISM: Artificial Sequence
<220> FEATURE:
<223> OTHER INFORMATION: pVP2 452 of IBDV Soroa strain

<400> SEQUENCE: 4

Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
```

-continued 145 150 155 160

Gly Glu Gly Val Thr Val Leu Ser Leu Pro Thr Ser Tyr Asp Leu Gly
165 170 175

Tyr Val Arg Leu Gly Asp Pro Ile Pro Ala Ile Gly Leu Asp Pro Lys
180 185 190

Met Val Ala Thr Cys Asp Ser Ser Asp Arg Pro Arg Val Tyr Thr Ile
195 200 205

Thr Ala Ala Asp Asp Tyr Gln Phe Ser Ser Gln Tyr Gln Pro Gly Gly
210 215 220

Val Thr Ile Thr Leu Phe Ser Ala Asn Ile Asp Ala Ile Thr Ser Leu
225 230 235 240

Ser Val Gly Gly Glu Leu Val Phe Arg Thr Ser Val His Gly Leu Val
245 250 255

Leu Gly Ala Thr Ile Tyr Leu Ile Gly Phe Asp Gly Thr Thr Val Ile
260 265 270

Thr Arg Ala Val Ala Ala Asn Asn Gly Leu Thr Thr Gly Thr Asp Asn
275 280 285

Leu Met Pro Phe Asn Leu Val Ile Pro Thr Asn Glu Ile Thr Gln Pro
290 295 300

Ile Thr Ser Ile Lys Leu Glu Ile Val Thr Ser Lys Ser Gly Gly Gln
305 310 315 320

Ala Gly Asp Gln Met Ser Trp Ser Ala Arg Gly Ser Leu Ala Val Thr
325 330 335

Ile His Gly Gly Asn Tyr Pro Gly Ala Leu Arg Pro Val Thr Leu Val
340 345 350

Ala Tyr Glu Arg Val Ala Thr Gly Ser Val Val Thr Val Ala Gly Val
355 360 365

Ser Asn Phe Glu Leu Ile Pro Asn Pro Glu Leu Ala Lys Asn Leu Val
370 375 380

Thr Glu Tyr Gly Arg Phe Asp Pro Gly Ala Met Asn Tyr Thr Lys Leu
385 390 395 400

Ile Leu Ser Glu Arg Asp Arg Leu Gly Ile Lys Thr Val Trp Pro Thr
405 410 415

Arg Glu Tyr Thr Asp Phe Arg Glu Tyr Phe Met Glu Val Ala Asp Leu
420 425 430

Asn Ser Pro Leu Lys Ile Ala Gly Ala Phe Gly Phe Lys Asp Ile Ile
435 440 445

Arg Ala Ile Arg
450

<210> SEQ ID NO 5
<211> LENGTH: 518
<212> TYPE: PRT
<213> ORGANISM: Artificial Sequence
<220> FEATURE:
<223> OTHER INFORMATION: fusion protein

<400> SEQUENCE: 5

Met Thr Asn Leu Ser Asp Gln Thr Gln Gln Ile Val Pro Phe Ile Arg
1 5 10 15

Ser Leu Leu Met Pro Thr Thr Gly Pro Ala Ser Ile Pro Asp Asp Thr
20 25 30

Leu Glu Lys His Thr Leu Arg Ser Glu Thr Ser Thr Tyr Asn Leu Thr
35 40 45

Val Gly Asp Thr Gly Ser Gly Leu Ile Val Phe Phe Pro Gly Phe Pro

-continued

```
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Arg Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg Pro Arg Asp Glu Ile Asp Gly Pro Ala Gly Gln
    450                 455                 460

Ala Glu Pro Asp Arg Ala His Tyr Asn Ile Val Thr Phe Cys Cys Lys
465                 470                 475                 480
```

```
Cys Asp Ser Thr Leu Arg Leu Cys Val Gln Ser Thr His Val Asp Ile
                485                 490                 495

Arg Thr Leu Glu Asp Leu Leu Met Gly Thr Leu Gly Ile Val Cys Pro
            500                 505                 510

Ile Cys Ser Gln Lys Pro
        515


<210> SEQ ID NO 6
<211> LENGTH: 54
<212> TYPE: PRT
<213> ORGANISM: Artificial Sequence
<220> FEATURE:
<223> OTHER INFORMATION: E7 of HPV-16 wherein amino acids 1 a 44 have
      been eliminated

<400> SEQUENCE: 6

Ala Glu Pro Asp Arg Ala His Tyr Asn Ile Val Thr Phe Cys Cys Lys
1               5                   10                  15

Cys Asp Ser Thr Leu Arg Leu Cys Val Gln Ser Thr His Val Asp Ile
            20                  25                  30

Arg Thr Leu Glu Asp Leu Leu Met Gly Thr Leu Gly Ile Val Cys Pro
        35                  40                  45

Ile Cys Ser Gln Lys Pro
    50


<210> SEQ ID NO 7
<211> LENGTH: 509
<212> TYPE: PRT
<213> ORGANISM: Artificial Sequence
<220> FEATURE:
<223> OTHER INFORMATION: fusion protein

<400> SEQUENCE: 7

Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190
```

-continued

Met Val Ala Thr Cys Asp Ser Ser Asp Arg Pro Arg Val Tyr Thr Ile
195 200 205

Thr Ala Ala Asp Asp Tyr Gln Phe Ser Ser Gln Tyr Gln Pro Gly Gly
210 215 220

Val Thr Ile Thr Leu Phe Ser Ala Asn Ile Asp Ala Ile Thr Ser Leu
225 230 235 240

Ser Val Gly Gly Glu Leu Val Phe Arg Thr Ser Val His Gly Leu Val
245 250 255

Leu Gly Ala Thr Ile Tyr Leu Ile Gly Phe Asp Gly Thr Thr Val Ile
260 265 270

Thr Arg Ala Val Ala Ala Asn Asn Gly Leu Thr Thr Gly Thr Asp Asn
275 280 285

Leu Met Pro Phe Asn Leu Val Ile Pro Thr Asn Glu Ile Thr Gln Pro
290 295 300

Ile Thr Ser Ile Lys Leu Glu Ile Val Thr Ser Lys Ser Gly Gly Gln
305 310 315 320

Ala Gly Asp Gln Met Ser Trp Ser Ala Arg Gly Ser Leu Ala Val Thr
325 330 335

Ile His Gly Gly Asn Tyr Pro Gly Ala Leu Arg Pro Val Thr Leu Val
340 345 350

Ala Tyr Glu Arg Val Ala Thr Gly Ser Val Val Thr Val Ala Gly Val
355 360 365

Ser Asn Phe Glu Leu Ile Pro Asn Pro Glu Leu Ala Lys Asn Leu Val
370 375 380

Thr Glu Tyr Gly Arg Phe Asp Pro Gly Ala Met Asn Tyr Thr Lys Leu
385 390 395 400

Ile Leu Ser Glu Arg Asp Arg Leu Gly Ile Lys Thr Val Trp Pro Thr
405 410 415

Arg Glu Tyr Thr Asp Phe Arg Glu Tyr Phe Met Glu Val Ala Asp Leu
420 425 430

Asn Ser Pro Leu Lys Ile Ala Gly Ala Phe Gly Phe Lys Asp Ile Ile
435 440 445

Arg Ala Ile Arg Arg Pro Arg Ala Glu Pro Asp Arg Ala His Tyr Asn
450 455 460

Ile Val Thr Phe Cys Cys Lys Cys Asp Ser Thr Leu Arg Leu Cys Val
465 470 475 480

Gln Ser Thr His Val Asp Ile Arg Thr Leu Glu Asp Leu Leu Met Gly
485 490 495

Thr Leu Gly Ile Val Cys Pro Ile Cys Ser Gln Lys Pro
500 505

<210> SEQ ID NO 8
<211> LENGTH: 525
<212> TYPE: PRT
<213> ORGANISM: Artificial Sequence
<220> FEATURE:
<223> OTHER INFORMATION: fusion protein

<400> SEQUENCE: 8

Met Thr Asn Leu Ser Asp Gln Thr Gln Gln Ile Val Pro Phe Ile Arg
1 5 10 15

Ser Leu Leu Met Pro Thr Thr Gly Pro Ala Ser Ile Pro Asp Asp Thr
20 25 30

Leu Glu Lys His Thr Leu Arg Ser Glu Thr Ser Thr Tyr Asn Leu Thr
35 40 45

-continued

```
Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Arg Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Met Arg Pro Gly Gly Gly Gly Ser Ala Glu Pro Asp
        435                 440                 445

Arg Ala His Tyr Asn Ile Val Thr Phe Cys Cys Lys Cys Asp Ser Thr
    450                 455                 460

Leu Arg Leu Cys Val Gln Ser Thr His Val Asp Ile Arg Thr Leu Glu
```

465 470 475 480

Asp Leu Leu Met Gly Thr Leu Gly Ile Val Cys Pro Ile Cys Ser Gln
485 490 495

Lys Pro Gly Gly Gly Gly Ser Thr Ser Gly Pro His Leu Lys Ile Ala
500 505 510

Gly Ala Phe Gly Phe Lys Asp Ile Ile Arg Ala Ile Arg
515 520 525

<210> SEQ ID NO 9
<211> LENGTH: 515
<212> TYPE: PRT
<213> ORGANISM: Artificial Sequence
<220> FEATURE:
<223> OTHER INFORMATION: fusion protein

<400> SEQUENCE: 9

Met Thr Asn Leu Ser Asp Gln Thr Gln Gln Ile Val Pro Phe Ile Arg
1 5 10 15

Ser Leu Leu Met Pro Thr Thr Gly Pro Ala Ser Ile Pro Asp Asp Thr
20 25 30

Leu Glu Lys His Thr Leu Arg Ser Glu Thr Ser Thr Tyr Asn Leu Thr
35 40 45

Val Gly Asp Thr Gly Ser Gly Leu Ile Val Phe Phe Pro Gly Phe Pro
50 55 60

Gly Ser Ile Val Gly Ala His Tyr Thr Leu Gln Gly Asn Gly Asn Tyr
65 70 75 80

Lys Phe Asp Gln Met Leu Leu Thr Ala Gln Asn Leu Pro Ala Ser Tyr
85 90 95

Asn Tyr Cys Arg Leu Val Ser Arg Ser Leu Thr Val Arg Ser Ser Thr
100 105 110

Leu Pro Gly Gly Val Tyr Ala Leu Asn Gly Thr Ile Asn Ala Val Thr
115 120 125

Phe Gln Gly Ser Leu Ser Glu Leu Thr Asp Val Ser Tyr Asn Gly Leu
130 135 140

Met Ser Ala Thr Ala Asn Ile Asn Asp Lys Ile Gly Asn Val Leu Val
145 150 155 160

Gly Glu Gly Val Thr Val Leu Ser Leu Pro Thr Ser Tyr Asp Leu Gly
165 170 175

Tyr Val Arg Leu Gly Asp Pro Ile Pro Ala Ile Gly Leu Asp Pro Lys
180 185 190

Met Val Ala Thr Cys Asp Ser Ser Asp Arg Pro Arg Val Tyr Thr Ile
195 200 205

Thr Ala Ala Asp Asp Tyr Gln Phe Ser Ser Gln Tyr Gln Pro Gly Gly
210 215 220

Val Thr Ile Thr Leu Phe Ser Ala Asn Ile Asp Ala Ile Thr Ser Leu
225 230 235 240

Ser Val Gly Gly Glu Leu Val Phe Arg Thr Ser Val His Gly Leu Val
245 250 255

Leu Gly Ala Thr Ile Tyr Leu Ile Gly Phe Asp Gly Thr Thr Val Ile
260 265 270

Thr Arg Ala Val Ala Ala Asn Asn Gly Leu Thr Thr Gly Thr Asp Asn
275 280 285

Leu Met Pro Phe Asn Leu Val Ile Pro Thr Asn Glu Ile Thr Gln Pro
290 295 300

Ile Thr Ser Ile Lys Leu Glu Ile Val Thr Ser Lys Ser Gly Gly Gln

```
305                 310                 315                 320

Ala Gly Asp Gln Met Ser Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Leu Arg Pro Ala Glu Pro Asp
        435                 440                 445

Arg Ala His Tyr Asn Ile Val Thr Phe Cys Cys Lys Cys Asp Ser Thr
    450                 455                 460

Leu Arg Leu Cys Val Gln Ser Thr His Val Asp Ile Arg Thr Leu Glu
465                 470                 475                 480

Asp Leu Leu Met Gly Thr Leu Gly Ile Val Cys Pro Ile Cys Ser Gln
                485                 490                 495

Lys Pro Thr Ser Gly Pro Gln Ala Phe Gly Phe Lys Asp Ile Ile Arg
            500                 505                 510

Ala Ile Arg
        515


<210> SEQ ID NO 10
<211> LENGTH: 515
<212> TYPE: PRT
<213> ORGANISM: Artificial Sequence
<220> FEATURE:
<223> OTHER INFORMATION: fusion protein

<400> SEQUENCE: 10

Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
```

-continued

```
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Arg Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Met Arg Pro Ala Glu Pro Asp Arg Ala His Tyr Asn Ile Val
    450                 455                 460

Thr Phe Cys Cys Lys Cys Asp Ser Thr Leu Arg Leu Cys Val Gln Ser
465                 470                 475                 480

Thr His Val Asp Ile Arg Thr Leu Glu Asp Leu Leu Met Gly Thr Leu
                485                 490                 495

Gly Ile Val Cys Pro Ile Cys Ser Gln Lys Pro Thr Ser Gly Pro Gln
            500                 505                 510

Ala Ile Arg
        515


<210> SEQ ID NO 11
<211> LENGTH: 516
<212> TYPE: PRT
<213> ORGANISM: Artificial Sequence
<220> FEATURE:
<223> OTHER INFORMATION: fusion protein
```

-continued

<400> SEQUENCE: 11

```
Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Arg Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415
```

```
Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Arg Pro Arg Asp Glu Ile Asp Gly Pro Ala Gly Gln Ala Glu
    450                 455                 460

Pro Asp Arg Ala His Tyr Asn Ile Val Thr Phe Cys Cys Lys Cys Asp
465                 470                 475                 480

Ser Thr Leu Arg Leu Cys Val Gln Ser Thr His Val Asp Ile Arg Thr
                485                 490                 495

Leu Glu Asp Leu Leu Met Gly Thr Leu Gly Ile Val Cys Pro Ile Cys
            500                 505                 510

Ser Gln Lys Pro
        515


<210> SEQ ID NO 12
<211> LENGTH: 515
<212> TYPE: PRT
<213> ORGANISM: Artificial Sequence
<220> FEATURE:
<223> OTHER INFORMATION: fusion protein

<400> SEQUENCE: 12

Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Arg Thr Ser Val His Gly Leu Val
                245                 250                 255
```

```
Leu Gly Ala Thr Ile Tyr Leu Ile Gly Phe Asp Gly Thr Thr Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Arg Pro Arg Asp Glu Ile Asp Gly Pro Ala Gly Gln Ala Glu Pro
    450                 455                 460

Asp Arg Ala His Tyr Asn Ile Val Thr Phe Cys Cys Lys Cys Asp Ser
465                 470                 475                 480

Thr Leu Arg Leu Cys Val Gln Ser Thr His Val Asp Ile Arg Thr Leu
                485                 490                 495

Glu Asp Leu Leu Met Gly Thr Leu Gly Ile Val Cys Pro Ile Cys Ser
            500                 505                 510

Gln Lys Pro
        515


<210> SEQ ID NO 13
<211> LENGTH: 512
<212> TYPE: PRT
<213> ORGANISM: Artificial Sequence
<220> FEATURE:
<223> OTHER INFORMATION: fusion protein

<400> SEQUENCE: 13

Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95
```

-continued

```
Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Arg Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Arg Pro
        435                 440                 445

Arg Asp Glu Ile Asp Gly Pro Ala Gly Gln Ala Glu Pro Asp Arg Ala
    450                 455                 460

His Tyr Asn Ile Val Thr Phe Cys Cys Lys Cys Asp Ser Thr Leu Arg
465                 470                 475                 480

Leu Cys Val Gln Ser Thr His Val Asp Ile Arg Thr Leu Glu Asp Leu
                485                 490                 495

Leu Met Gly Thr Leu Gly Ile Val Cys Pro Ile Cys Ser Gln Lys Pro
            500                 505                 510
```

<210> SEQ ID NO 14
<211> LENGTH: 509
<212> TYPE: PRT
<213> ORGANISM: Artificial Sequence
<220> FEATURE:
<223> OTHER INFORMATION: fusion protein

<400> SEQUENCE: 14

```
Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Arg Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365
```

-continued

```
Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Arg Pro Arg Asp Glu
        435                 440                 445

Ile Asp Gly Pro Ala Gly Gln Ala Glu Pro Asp Arg Ala His Tyr Asn
    450                 455                 460

Ile Val Thr Phe Cys Cys Lys Cys Asp Ser Thr Leu Arg Leu Cys Val
465                 470                 475                 480

Gln Ser Thr His Val Asp Ile Arg Thr Leu Glu Asp Leu Leu Met Gly
                485                 490                 495

Thr Leu Gly Ile Val Cys Pro Ile Cys Ser Gln Lys Pro
            500                 505


<210> SEQ ID NO 15
<211> LENGTH: 507
<212> TYPE: PRT
<213> ORGANISM: Artificial Sequence
<220> FEATURE:
<223> OTHER INFORMATION: fusion protein

<400> SEQUENCE: 15

Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220
```

-continued

Val Thr Ile Thr Leu Phe Ser Ala Asn Ile Asp Ala Ile Thr Ser Leu
225 230 235 240

Ser Val Gly Gly Glu Leu Val Phe Arg Thr Ser Val His Gly Leu Val
245 250 255

Leu Gly Ala Thr Ile Tyr Leu Ile Gly Phe Asp Gly Thr Thr Val Ile
260 265 270

Thr Arg Ala Val Ala Ala Asn Asn Gly Leu Thr Thr Gly Thr Asp Asn
275 280 285

Leu Met Pro Phe Asn Leu Val Ile Pro Thr Asn Glu Ile Thr Gln Pro
290 295 300

Ile Thr Ser Ile Lys Leu Glu Ile Val Thr Ser Lys Ser Gly Gly Gln
305 310 315 320

Ala Gly Asp Gln Met Ser Trp Ser Ala Arg Gly Ser Leu Ala Val Thr
325 330 335

Ile His Gly Gly Asn Tyr Pro Gly Ala Leu Arg Pro Val Thr Leu Val
340 345 350

Ala Tyr Glu Arg Val Ala Thr Gly Ser Val Val Thr Val Ala Gly Val
355 360 365

Ser Asn Phe Glu Leu Ile Pro Asn Pro Glu Leu Ala Lys Asn Leu Val
370 375 380

Thr Glu Tyr Gly Arg Phe Asp Pro Gly Ala Met Asn Tyr Thr Lys Leu
385 390 395 400

Ile Leu Ser Glu Arg Asp Arg Leu Gly Ile Lys Thr Val Trp Pro Thr
405 410 415

Arg Glu Tyr Thr Asp Phe Arg Glu Tyr Phe Met Glu Val Ala Asp Leu
420 425 430

Asn Ser Pro Leu Lys Ile Ala Gly Ala Arg Pro Arg Asp Glu Ile Asp
435 440 445

Gly Pro Ala Gly Gln Ala Glu Pro Asp Arg Ala His Tyr Asn Ile Val
450 455 460

Thr Phe Cys Cys Lys Cys Asp Ser Thr Leu Arg Leu Cys Val Gln Ser
465 470 475 480

Thr His Val Asp Ile Arg Thr Leu Glu Asp Leu Leu Met Gly Thr Leu
485 490 495

Gly Ile Val Cys Pro Ile Cys Ser Gln Lys Pro
500 505

<210> SEQ ID NO 16
<211> LENGTH: 513
<212> TYPE: PRT
<213> ORGANISM: Artificial Sequence
<220> FEATURE:
<223> OTHER INFORMATION: fusion protein

<400> SEQUENCE: 16

Met Thr Asn Leu Ser Asp Gln Thr Gln Gln Ile Val Pro Phe Ile Arg
1 5 10 15

Ser Leu Leu Met Pro Thr Thr Gly Pro Ala Ser Ile Pro Asp Asp Thr
20 25 30

Leu Glu Lys His Thr Leu Arg Ser Glu Thr Ser Thr Tyr Asn Leu Thr
35 40 45

Val Gly Asp Thr Gly Ser Gly Leu Ile Val Phe Phe Pro Gly Phe Pro
50 55 60

Gly Ser Ile Val Gly Ala His Tyr Thr Leu Gln Gly Asn Gly Asn Tyr
65 70 75 80

-continued

```
Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Arg Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg Pro Arg Pro Ala Gly Gln Ala Glu Pro Asp Arg
    450                 455                 460

Ala His Tyr Asn Ile Val Thr Phe Cys Cys Lys Cys Asp Ser Thr Leu
465                 470                 475                 480

Arg Leu Cys Val Gln Ser Thr His Val Asp Ile Arg Thr Leu Glu Asp
                485                 490                 495

Leu Leu Met Gly Thr Leu Gly Ile Val Cys Pro Ile Cys Ser Gln Lys
```

500 505 510

Pro

<210> SEQ ID NO 17
<211> LENGTH: 512
<212> TYPE: PRT
<213> ORGANISM: Artificial Sequence
<220> FEATURE:
<223> OTHER INFORMATION: fusion protein

<400> SEQUENCE: 17

```
Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Arg Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350
```

```
Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg Pro Arg Ala Gly Gln Ala Glu Pro Asp Arg Ala
    450                 455                 460

His Tyr Asn Ile Val Thr Phe Cys Cys Lys Cys Asp Ser Thr Leu Arg
465                 470                 475                 480

Leu Cys Val Gln Ser Thr His Val Asp Ile Arg Thr Leu Glu Asp Leu
                485                 490                 495

Leu Met Gly Thr Leu Gly Ile Val Cys Pro Ile Cys Ser Gln Lys Pro
            500                 505                 510


<210> SEQ ID NO 18
<211> LENGTH: 1151
<212> TYPE: DNA
<213> ORGANISM: Artificial Sequence
<220> FEATURE:
<223> OTHER INFORMATION: Cloning insert

<400> SEQUENCE: 18

gactgcggcc gccctatcgt caattattac ctccacgggg agagcctgag caaactggcc      60

tcaggcattt gagaagcaca cggtcacact gcttccggta gtcaataaac cggtaaacca     120

gcaatagaca taagcggcta tttaacgacc ctgccctgaa ccgacgaccg ggtcgaattt     180

gctttcgaat ttctgccatt catccgctta ttatcactta ttcaggcgta gcaaccaggc     240

gtttaagggc accaataact gccttaaaaa aattacgccc cgccctgcca ctcatcgcag     300

tactgttgta attcattaag cattctgccg acatggaagc catcacaaac ggcatgatga     360

acctgaatcg ccagcggcat cagcaccttg tcgccttgcg tataatattt gcccatggtg     420

aaaacggggg cgaagaagtt gtccatattg gccacgttta aatcaaaact ggtgaaactc     480

acccagggat tggctgagac gaaaaacata ttctcaataa accctttagg gaaataggcc     540

aggttttcac cgtaacacgc cacatcttgc gaatatatgt gtagaaactg ccggaaatcg     600

tcgtggtatt cactccagag cgatgaaaac gtttcagttt gctcatggaa aacggtgtaa     660

caagggtgaa cactatccca tatcaccagc tcaccgtctt tcattgccat acgtaattcc     720

ggatgagcat tcatcaggcg ggcaagaatg tgaataaagg ccggataaaa cttgtgctta     780

tttttcttta cggtctttaa aaaggccgta atatccagct gaacggtctg gttataggta     840

cattgagcaa ctgactgaaa tgcctcaaaa tgttctttac gatgccattg ggatatatca     900

acggtggtat atccagtgat ttttttctcc attttagctt ccttagctcc tgaaaatctc     960

gacaactcaa aaaatacgcc cggtagtgat cttatttcat tatggtgaaa gttggaacct    1020

cttacgtgcc gatcaacgtc tcattttcgc caaaagttgg cccagggctt cccggtatca    1080

acagggacac caggatttat ttattctgcg aagtgatctt ccgtcacagg tatttactag    1140
```

-continued

```
tgggcccagt c                                                          1151


<210> SEQ ID NO 19
<211> LENGTH: 180
<212> TYPE: DNA
<213> ORGANISM: Artificial Sequence
<220> FEATURE:
<223> OTHER INFORMATION: Insert HPV-16 E7 with amino acids 1-44
      eliminated

<400> SEQUENCE: 19

ccagggcccg ctgaaccaga tagagcccat tacaacattg tcacattctg ttgtaaatgt      60

gattcaacat tgagattatg tgttcaatct acccatgttg atattagaac attagaagat     120

ttgttaatgg gtacattagg tattgtttgt ccaatttgct cacaaaaacc tactagtggt     180


<210> SEQ ID NO 20
<211> LENGTH: 211
<212> TYPE: DNA
<213> ORGANISM: Artificial Sequence
<220> FEATURE:
<223> OTHER INFORMATION: Insert HPV-16 E7 with amino acids 1-44
      eliminated and linker

<400> SEQUENCE: 20

ccagggcccg gtggtggagg ttcagctgaa ccagatagag cccattacaa cattgtcaca      60

ttctgttgta aatgtgattc aacattgaga ttatgtgttc aatctaccca tgttgatatt     120

agaacattag aagatttgtt aatgggtaca ttaggtattg tttgtccaat ttgctcacaa     180

aaacctggag gaggtggatc aactagtggt c                                    211


<210> SEQ ID NO 21
<211> LENGTH: 5
<212> TYPE: PRT
<213> ORGANISM: Artificial Sequence
<220> FEATURE:
<223> OTHER INFORMATION: sequence of linker

<400> SEQUENCE: 21

Gly Gly Gly Gly Ser
1               5
```

VACCINES FOR THE TREATMENT OF NEOPLASIAS FROM VIRAL CAPSIDS OF BIRNAVIRUS CONTAINING ANTIGENS OF THE HUMAN PAPILLOMAVIRUS

This application is the U.S. national phase of International Patent Application No. PCT/ES2010/070717, filed Nov. 5, 2010, which claims the benefit of Spanish Patent Application No. P200930967, filed Nov. 6, 2009.

The invention relates to therapeutic vaccines for the treatment of neoplasias caused by the human papillomavirus (HPV). In particular, the vaccines of the present invention are formed by chimeric virus-like capsids of birnavirus containing papillomavirus antigens.

PRIOR ART

Human papillomaviruses (HPV) are the main causes of development of intrauterine neoplasms and are frequently associated to other neoplasias such as anal cancer, vulvar cancer, cancer of the penis or oropharyngeal squamous cell carcinoma. HPV infections can go unnoticed for years until they may appear in the form of local neoplasias in varying degrees of progression. This is why regular smear tests are performed on women with a view to identify pre-malignant cells and where applicable the type of causing virus. The most common strains of HPV associated to local intrauterine neoplasias are HPV-16 and HPV-18, involved in 70% of all cases of cervical cancer. The oncogenic effect of these HPV is mediated by the integration of part of its genome, in particular of the early expression genes E6 and E7, in the genome of the infected basal epithelial cells.

There are currently prophylactic vaccines on the market to prevent infection by the papillomavirus such as Gardasil® and Cervarix® for example. These vaccines are effective in preventing infection by human papillomavirus strains HPV-16, HPV-18, HPV-11 and HPV-6, but their efficiency in a therapeutic context has not been proven once the HPV has transformed the infected cell into a pre-cancerous cell.

It is estimated that in just the US, 10 million women are in contact with HPV every year and it is predicted that 23% of these women will develop local intrauterine neoplasias (or CIN, Cervical Intrauterine Neoplasias) to some degree, at some point in their life [Hoory T et al. (2008) J. Formos Med. Assoc 107(3):198-217]. Furthermore, every year 275,000 women die in the world due to cervical cancer as a result of the unfavourable development of a CIN. Although currently cervical cancer prevention and monitoring programmes by means of regular gynaecological check-ups and surgical removal of CIN are effective, it would be desirable to count on a non-invasive therapeutic approach that would prevent surgery-related costs and potential complications.

There are precedents in the development of therapeutic vaccines for the treatment of CIN that incorporate E6 and/or E7 antigens of the papillomavirus [Lin Y. et al. (2007) Frontier in Bioscience, 12: 246-264; Leggatt G R et al. (2007) Current Opin. Immunology, 19: 232-238; Hung C F et al. (2007) Exp. Mol. Med, 39(6):679-689; Hoory T et al. (2008) J. Formos Med. Assoc, 107(3):198-217]. These include DNA vaccines [Yan Q. et al (2007) Gynecologic Onco., 104:199-206; Yan J. et al. (2009) Vaccine, 27:431-440], vaccines based on naked peptides [Daffarin P M. et al (2007) J. Translational Med., 5:26; Toubaji A. et al. (2007) Vaccine, 25: 5882-5891; Smith K A. et al. (2009) Clin. Cancer Res. 15(19):6167-6176], and vaccines wherein the HPV antigens are linked or fused to other biological entities, such as for example the adenylate cyclase of *Bordetella pertussis* [Preville X. et al. (2005) Cancer Res., 65(2):641-649], antigen 4 of cytotoxic T lymphocytes (CTLA4) [Zheng Y. et al. (2009) J. Microbiol., 46(6):728-736] or 1,3-1,4 beta-glucanase of *Clostridium thermocellum* [Venuti A. et al. (2009) Vaccine, 27 (25-26): 3395-3397]. In the case of vaccines using the presentation of antigens on biological macrostructures, one example consists of chimeric virus-like particles (VLP) formed on the basis of structural viral proteins that incorporate antigens relevant to a disease. In this sense there are precedents that incorporate E7 antigens in VLP of Hepatitis B [Tindle R W. et al. Virology (1994) 1; 200(2):547-57]. Among the VLP proposed for antigen presentation are those deriving from the Infectious Bursal Disease Virus (IBDV). IBDV belongs to the Birnaviridae family and is the agent responsible for causing Gumboro disease in birds. The viral particles of IBDV are icosahedral with a symmetry of T=13 and are formed by 260 trimers of the protein VP2 (37 kDa) reinforced on its internal side by the structural protein VP3 (29 kDa). In the normal assembly of the virion, the protein components of the viral capsid result from proteolysis of the precursor polypeptide pVP2-VP4-VP3 (109 kDa) to release the VP2 precursor of 512 amino acids ($pVP2_{512}$), VP4 and VP3. The subsequent removal of amino acids in the carboxyl terminal of $pVP2_{512}$ gives rise to the mature form of VP2 of 441 amino acids ($VP2_{441}$) present in the virion [Da Costa B. et al. J. Virology (2002) 76(5): 2393-2402]. The VP2 found in different strains of IBDV presents a protein sequence homology of more than 80%. The VP2 of other Birnaviridae share with IBDV protein sequence homologies of about 40% in the case of aquatic Birnavirus and 30% in *Drosophila* Birnavirus [Coulibaly F. et al. (2005) Cell 25, 120(6):761-772].

The expression of the precursor polypeptide pVP2-VP4-VP3 of IBDV in eukaryotic cells results in the formation of icosahedral VLP with symmetry T=13, identical to the native capsids of IBDV [Martinez-Torrecuadrada J L. et al. (2001) J. Virology 75(22):10815-10828]. At the same time, the expression of VP2 in eukaryotic cells in the absence of other proteins of IBDV results in the formation of icosahedral VLP with symmetry T=1 smaller than those comprising the IBDV [Martinez-Torrecuadrada J L. et al. (2003) Vaccine 21(17-18):1952-1960]. This has been used in the design and expression of chimeric VLP that incorporate the BT antigen of foot and mouth disease in VLP T=1 based on fusions in the carboxyl terminus of VP2 [WO2007009673].

The capacity of fusions or insertions of VP2 to form VLP T=1 efficiently in a eukaryotic expression system depends to a great extent on the length of the VP2 [WO2005105834; Saugar I. et al. (2005) Structure 13(7):1007-1117], on the place of insertion of these inserts in the VP2 sequence, and on the sequence of the inserts introduced in VP2 [Rémond M. et al (2009) Vaccine. 27(1):93-8]. However, the capacity of the obtained chimeric VLP to induce a suitable immune response in an animal model is unpredictable.

DESCRIPTION OF THE INVENTION

In the design of therapeutic vaccines against HPV it would be desirable to have a HPV antigen presentation system that generated a specific and effective cellular immune response. The present invention combines sequences of VP2 of IBDV and of E7 of HPV with a view to obtaining an effective therapeutic vaccine for the treatment of tumours induced by HPV. It is not obvious which sequences of E7 or VP2 may be ideal in the generation of the vaccine, nor the ideal place of fusion or insertion of E7 with VP2. For this reason, in the present invention a search process is carried out of chimeric VLP T=1 based on fusions and insertions of E7 in VP2 of IBDV resulting in the selection of the most effective chimeric VLP in the treatment of lesions caused by HPV.

The object of the invention is to provide a vaccine that is effective in the treatment of neoplasias caused by the human papillomavirus. The therapeutic vaccines of the present invention consist of chimeric virus-like particles formed on the basis of fusions and insertions of sequences of the E7 protein of human HPV and sequences of VP2 of the infectious bursal disease virus. The search and selection process carried out results in viral-like particles based on fusions and insertions of $E7_{\Delta 1\text{-}44}$ of HPV with $VP2_{452}$ of IBDV with greater antitumoral efficacy and object of the present invention.

The present invention relates to chimeric virus-like particles (VLP) based on birnavirus VP2 that incorporate sequences of HPV oncogenes. The fusion or insertion of sequences not related to birnavirus in VP2 often results in modifications of the three-dimensional structure of the protein which negatively affect its capacity to self-assemble and form virus-like capsids in an efficient manner. This negative effect not only depends on the insertion point, but also on the amino acid sequence and length of the insert. Therefore it is not obvious a priori which insertion points and inserted amino acid sequences result in an efficient formation of chimeric VLP. At the same time, the formation of VLP that incorporate oncogenic sequences of HPV is not a sufficient condition to generate an efficient therapeutic vaccine against tumours, this depends on the final arrangement of the E7 antigens on the formed chimeric VLP.

The chimeric VLP of the present invention are obtained from a selection process wherein optimum sequences of E7 for the formation of VLP are identified and the places of fusion or insertion in VP2 that give rise to chimeric VLP of greater efficacy in the treatment of tumours expressing oncogenic proteins E6 and E7 of HPV-16.

In the first place, as described without limitation in Example 1, fusions are evaluated of truncated sequences of E7 to the carboxyl terminal end of sequences of VP2 truncated at the carboxyl terminus. Among others, fusions of sequences of E7 are evaluated wherein amino acids 1 to 35 have been eliminated ($E7_{\Delta 1\text{-}35}$) [SEQ ID NO: 3] to the carboxyl end of the VP2 truncated at the carboxyl end starting from amino acid 452 ($VP2_{452}$) [SEQ ID NO: 4]. In order to improve the expression, various fusions are also evaluated of $E7_{\Delta 1\text{-}35}$ to the carboxyl terminus of $VP2_{441}$, $VP2_{443}$, $VP2_{446}$ $VP2_{449}$ and $VP2_{450}$ resulting from the elimination of amino acids from the carboxyl terminal end of $VP2_{452}$. No case exceeds the efficiency in the production of chimeric VLP of the fusions $VP2_{452}$-$E7_{\Delta 1\text{-}35}$ [SEQ ID NO: 5]. In order to select the sequences of E7 that fused to the carboxyl terminal end of VP2 give rise to a greater expression, fusions are evaluated to the carboxyl terminal end of $VP2_{452}$ of the following truncated E7 sequences: $E7_{\Delta 1\text{-}40}$, $E7_{\Delta 1\text{-}41}$, $E7_{\Delta 1\text{-}44}$. The fusion of truncated E7 $E7_{\Delta 1\text{-}44}$ [SEQ ID NO: 6] with the Arginine (R) of the carboxyl terminal end of $VP2_{452}$ [SEQ ID NO: 4] results in a construction $VP2_{452}$-$E7_{\Delta 1\text{-}44}$ [SEQ ID NO: 7] with an efficiency in the production of chimeric VLP superior to others evaluated. At the same time, VLP with the amino acid sequence $VP2_{452}$-$E7_{\Delta 1\text{-}44}$ prove to be effective in the elimination of tumours that express proteins E6 and E7 of HPV-16 in animal models and represent a preferred embodiment of the present invention. Therefore, the present invention incorporates chimeric virus-like particles based on sequences of E7 of HPV-16 from which amino acids 1 to 44 have been eliminated ($E7_{\Delta 1\text{-}44}$), fused to the carboxyl terminal end of VP2 truncated in the carboxyl end from amino acid 452 ($VP2_{452}$). It is contemplated that these fusions may contain variations or insertions in their amino acid sequence of 7, and up to 10 amino acids, in particular in the points of fusion between $VP2_{452}$ and $E7_{\Delta 1\text{-}44}$ and as a result of the use of cloning sequences.

In second place, and as described without limitation in Example 2, random insertions are evaluated of sequences of E7 in HPV-16 wherein amino acids 1 to 44 have been eliminated ($E7_{\Delta 1\text{-}44}$) [SEQ ID NO: 6] in different points in the sequence of VP2 truncated in the carboxyl end from amino acid 452 ($VP2_{452}$) [SEQ ID NO: 4]. The process of identification and selection of the candidates with a greater potential for efficacy in the treatment of subcutaneous tumours expressing oncogenic proteins E6 and E7 of HPV-16 is carried out according to the following steps. In a first step, random insertions are made of $E7_{\Delta 1\text{-}44}$ in VP2 and all those constructions that do not result in the efficient expression of VLP are eliminated. In a second step, a selection process is carried out of the candidates that produce VLP efficiently and that prove to contain the sequences of $E7_{\Delta 1\text{-}44}$. In a third step, those chimeric VLP that generate a significant cellular immune response against protein E7 are selected. In a fourth step, the capacity of the selected chimeric VLP to provide an antitumoral effect in an animal model of neoplasia associated to the expression of E7 is evaluated. As a final result of the process, three chimeric VLP are selected which represent a preferred embodiment of the present invention, which are $VP2_{452}(L_{436}\uparrow E7_{\Delta 1\text{-}44}\uparrow K_{437})$ wherein the sequence of $E7_{\Delta 1\text{-}44}$ is inserted between Leucine (L) in position 436 and Lysine (K) in position 437 of $VP2_{452}$ [SEQ ID NO: 8]; $VP2_{452}(A_{441}\uparrow E7_{\Delta 1\text{-}44}\uparrow F_{442})$ wherein the sequence of $E7_{\Delta 1\text{-}44}$ is inserted between Alanine (A) in position 441 and Phenylalanine (F) in position 442 of $VP2_{452}$ [SEQ ID NO: 9]; and $VP2_{452}(A_{450}\uparrow E7_{\Delta 1\text{-}44}\uparrow I_{451})$ wherein the sequence of $E7_{\Delta 1\text{-}44}$ is inserted between Alanine (A) in position 450 and Isoleucine (I) in position 451 of $VP2_{452}$ [SEQ ID NO: 10].

Therefore, the present invention describes chimeric virus-like particles based on sequences of E7 of HPV-16 wherein amino acids 1 to 44 have been eliminated ($E7_{\Delta 1\text{-}44}$), inserted in the VP2 truncated in the carboxyl end from amino acid 452 ($VP2_{452}$) in positions $L_{436}\uparrow K_{437}$, $A_{441}\uparrow F_{442}$ and $A_{450}\uparrow I_{451}$. It is contemplated that these fusions contain variations or insertions in their sequence of up to 15 amino acids at each end of the insert, in particular in the fusion points between $VP2_{452}$ and $E7_{\Delta 1\text{-}44}$, as a result of the use of cloning sequences and as a result of the addition of linkers that increase the flexibility of the insertion.

A first aspect of the invention relates to a chimeric virus-like particle (VLP) (hereinafter, chimeric VLP of the invention) formed by a fusion protein (hereinafter, fusion protein of the invention) which comprises:

- a subunit (a) consisting of the protein pVP2 of Birnavirus or a fragment thereof, and
- a subunit (b) consisting of early expression protein E6 or E7 of the human papillomavirus (HPV) or a fragment thereof.

The term “virus-like capsid”, “virus-like particle” or “VLP” refers to a three-dimensional nanometric structure formed by the assembly of structural viral proteins. In the present invention, the structural viral proteins forming the virus-like particle of the invention are fusion proteins that comprise the pVP2 protein of a Birnavirus or a fragment thereof and an early expression protein E6 or E7 of HPV or a fragment thereof.

The term Birnavirus refers to any virus of the Birnaviridae family, belonging to Group III according to the Baltimore Classification. The Birnaviridae family consists of the *Avibirnavirus, Aquabirnavirus, Blosnavirus* and *Entomobirnavirus* genuses. Preferably, the Birnavirus is of the *Avibirnavirus* family, and more preferably, is the Infectious Bursal Disease Virus (IBDV).

The term "infectious bursal disease virus" or "IBDV" refers to viruses of the Birnaviridae family and *Avibirnavirus* genus causing Gumboro disease in chicken and belonging to Group III of the Baltimore Classification. Preferably, the IBDV is the Soroa strain IBDV.

The Birnavirus genome is formed by two linear molecules of double-stranded RNA referred to as A and B, encoding 5 proteins. Gene VP2, embedded in segment A, encodes the precursor protein of protein VP2 (pVP2). The elimination of the carboxyl terminal end of pVP2 by proteolysis gives rise to the mature VP2 protein, which is the main protein the viral capsid consists of.

The term "pVP2 protein" or "pVP2", as used in the present description, refers to the precursor protein of VP2 encoded by the gene VP2 of a Birnavirus. Preferably, this term refers to the precursor protein of VP2 of 512 amino acids ($VP2_{512}$) of IBDV.

The amino acid sequence of protein $VP2_{512}$ of the Soroa strain IBDV (SEQ ID NO: 1) is deposited with access number AAD30136 in the NCBI (*National Center for Biotechnology Information*). Protein $VP2_{512}$ in other strains of IBDV presents at least 80% identity with SEQ ID NO: 1. Therefore, in a preferred embodiment, the term pVP2 refers to a protein having at least 80%, 85%, 90%, 95%, 98% or 99% identity, with SEQ ID NO: 1. In a more preferred embodiment, the term pVP2 refers to SEQ ID NO: 1.

The term "identity" as used in this description, refers to the proportion of identical amino acids between two compared sequences of amino acids. The percentage of identity that exists between two amino acid sequences can be easily identified by a person skilled in the art, for example using a suitable sequence comparison software.

The term "fragment", as used in the present description, refers to a portion of the pVP2 protein, of at least 400 amino acids, capable of forming VLP. This term therefore includes the mature VP2 protein of 441 amino acids of IBDV ($VP2_{441}$).

In a preferred embodiment of this first aspect of the invention, subunit (a) of the fusion protein that forms the chimeric VLP of the invention consists of a protein having at least 80% identity with SEQ ID NO: 1 or a fragment thereof. In a more preferred embodiment, subunit (a) of the fusion protein that forms the chimeric VLP of the invention consists of a protein having SEQ ID NO: 1 or a fragment thereof. In an even more preferred embodiment, subunit (a) of the fusion protein that forms the chimeric VLP of the invention consists of SEQ ID NO: 4.

The term "human papillomavirus" or "HPV" refers to a virus of the Papillomaviridae family belonging to Group I of the Baltimore Classification, and therefore having a double-stranded DNA genome. More than 100 different types of human papillomavirus are known. The strains of HPV most frequently associated to intrauterine neoplasia are HPV-16 and HPV-18. The oncogenic effect of these HPV is mediated by the integration of part of its genome, in particular early expression genes E6 and E7, in the genome of the infected basal epithelial cells.

The term "early expression protein E6", "early expression oncogene E6" or "E6" refers to the protein encoded by the early expression gene E6 of a HPV, and more preferably, of HPV-16 or HPV-18.

The term "early expression protein E7", "early expression oncogene E7" or "E7" refers to a protein encoded by the early expression gene E7 of a HPV, and more preferably, of HPV-16 or HPV-18.

The prototypical sequence of amino acids of the early expression protein E7 of HPV type 16 [SEQ ID NO: 2] is deposited with access number NP_041326 in the NCBI. Therefore, in a preferred embodiment, the term early expression protein E7 refers to a protein having at least 30%, 40%, 50%, 70%, 90%, 95%, 98%, or 99% identity, with SEQ ID NO: 2. In a more preferred embodiment, the term early expression protein E7 of HPV refers to SEQ ID NO: 2.

In another preferred embodiment of this first aspect of the invention, subunit (b) of the fusion protein that forms the chimeric VLP of the invention consists of a protein having at least 30% identity with SEQ ID NO: 2 or a fragment thereof. In a more preferred embodiment, subunit (b) of the fusion protein that forms the chimeric VLP of the invention consists of a protein with SEQ ID NO: 2 or a fragment thereof. In an even more preferred embodiment, subunit (b) of the fusion protein that forms the chimeric VLP of the invention consists of SEQ ID NO: 6.

In another preferred embodiment of this first aspect of the invention, subunit (b) is joined to the carboxyl-terminal end of the subunit (a) in order to give rise to the fusion protein that forms the chimeric VLP of the invention. This link may be direct or by means of a linker polypeptide.

The term "linker polypeptide" or "linker" as used in the present description, refers to a short amino acid sequence, preferably, of up to 20 amino acids in length, more preferably, of up to 15 amino acids in length, and even more preferably, of up to 10 amino acids in length, situated between the sequence of amino acids of subunit (b) and the sequence of amino acids of subunit (a).

When the link is direct between subunits (a) and (b) of the fusion protein that forms the VLP of the invention, the amino acid of the carboxyl-terminal end of subunit (a) forms a peptide bond with the amino acid of the amino-terminal end of subunit (b), as shown in the following diagram:

Nt-(a)-Ct~Nt-(b)-Ct wherein (a) represents subunit (a), (b) represents subunit (b), Nt represents the amino-terminal end of the corresponding subunit, Ct represents the carboxyl-terminal end of the corresponding subunit, and ~ represents a peptide bond between the different units of the fusion protein of the invention.

When the bond between subunits (a) and (b) of the fusion protein that forms the VLP of the invention is carried out using a polypeptide linker, the amino acid of the carboxyl-terminal end of subunit (a) forms a peptide bond with the amino acid of the amino-terminal end of the linker peptide (p) and the amino acid of the carboxyl-terminal end of the linker polypeptide forms a bond with the amino acid of the amino-terminal end of subunit (b), as shown in the following diagram:

Nt-(a)-Ct~Nt-(p)-Ct~Nt-(b)-Ct wherein (a) represents subunit (a), (b) represents subunit (b), (p) represents the linker polypeptide, Nt represents the amino-terminal end of the corresponding subunit or linker polypeptide, Ct represents the carboxyl-terminal end of the corresponding subunit or linker polypeptide, and ~ represents a peptide bond between the different units of the fusion protein of the invention.

In another preferred embodiment, subunit (b) is inserted in subunit (a) to give rise to the fusion protein that forms the chimeric VLP of the invention. The expression "inserted" means that the sequence of amino acids of subunit (a) is divided into two parts (a1) and (a2), between which the sequence of amino acids of subunit (b) is found.

When the bond between subunits (a) and (b) of the fusion protein that forms the VLP of the invention is direct, the amino acid of the carboxyl-terminal end of part (a1) of subunit (a) forms a peptide bond with the amino acid of the amino-terminal end of subunit (b) and the amino acid of the carboxyl-terminal end of subunit (b) forms a peptide bond with the amino acid of the amino-terminal end of part (a2) of subunit (a), as shown in the following diagram:

Nt-(a1)-Ct~Nt-(b)-Ct~Nt-(a2)-Ct wherein (a1) represents a part of subunit (a), (a2) represents the other part of subunit (a), (b) represents subunit (b), Nt represents the amino-terminal end of the corresponding subunit, Ct represents the carboxyl-terminal end of the corresponding subunit, and ~ represents a peptide bond between the different units of the fusion protein of the invention.

When the bond between subunits (a) and (b) of the fusion protein that forms the VLP of the invention is achieved by means of two linker polypeptides, which may be identical or different, the amino acid of the carboxyl-terminal end of part (a1) of subunit (a) forms a peptide bond with the amino acid of the amino-terminal end of a first linker polypeptide (p1), the amino acid of the carboxyl-terminal end of this first linker polypeptide (p1) forms a bond with the amino acid of the amino-terminal end of subunit (b), the amino acid of the carboxyl-terminal end of subunit (b) forms a peptide bond with the amino acid of the amino-terminal end of a second linker polypeptide (p2) and the amino acid of the carboxyl-terminal end of this second linker polypeptide (p2) forms a bond with the amino acid of the amino-terminal end of part (a2) of subunit (a), as shown in the following diagram:

Nt-(a1)-Ct~Nt-(p1)-Ct~Nt-(b)-Ct~Nt-(p2)-Ct~Nt-(a2)-Ct wherein (a1) represents a part of subunit (a), (a2) represents the other part of subunit (a), (b) represents subunit (b), (p1) represents a first linker polypeptide, (p2) represents a second linker polypeptide, Nt represents the amino-terminal end of the corresponding subunit or linker polypeptide, Ct represents the carboxyl-terminal end of the corresponding subunit or linker polypeptide, and ~ represents a peptide bond between the different units of the fusion protein of the invention.

When the bond between subunits (a) and (b) of the fusion protein that forms the VLP of the invention is achieved by means of one linker polypeptide only, subunit (b) is linked at one end with one of the parts of subunit (a) directly by means of a peptide bond, and at the other end is linked with the other part of subunit (a) by means of a linker polypeptide, as shown in the following diagrams:

Nt-(a1)-Ct~Nt-(b)-Ct~Nt-(p)-Ct~Nt-(a2)-Ct

Nt-(a1)-Ct~Nt-(p)-Ct~Nt-(b)-Ct~Nt-(a2)-Ct wherein (a1) represents one part of subunit (a), (a2) represents the other part of subunit (a), (b) represents subunit (b), (p) represents a linker polypeptide, Nt represents the amino-terminal end of the corresponding subunit or linker polypeptide, Ct represents the carboxyl-terminal end of the corresponding subunit or linker polypeptide, and ~ represents a peptide bond between the different units of the fusion protein of the invention.

A preferred embodiment of this first aspect of the invention, relates to a chimeric VLP formed by a fusion protein comprising SEQ ID NO: 4 and SEQ ID NO: 6. A more preferred embodiment, relates to a chimeric VLP formed by a fusion protein comprising SEQ ID NO: 4 and SEQ ID NO: 6, and additionally comprising one or more linker polypeptides of up to 15 amino acids.

A more preferred embodiment of this first aspect of the invention, relates to a chimeric VLP formed by a fusion protein comprising SEQ ID NO: 4 and SEQ ID NO: 6, wherein SEQ ID NO: 6 is linked to the carboxyl-terminal end of SEQ ID NO: 4 by means of a peptide bond between the Arginine of position 452 ($R_{452}$) of SEQ ID NO: 4 and the Alanine of position 1 (A1) of SEQ ID NO: 6.

Another more preferred embodiment of this first aspect of the invention, relates to a chimeric VLP formed by a fusion protein comprising SEQ ID NO: 4 and SEQ ID NO: 6, wherein SEQ ID NO: 6 is linked to the carboxyl end of SEQ ID NO: 4, and additionally comprising a linker polypeptide of up to 10 amino acids between SEQ ID NO: 4 and SEQ ID NO: 6. This linker polypeptide is linked by its amino-terminal end with the Arginine of position 452 ($R_{452}$) of SEQ ID NO: 4 and by its carboxyl-terminal end with the Alanine of position 1 (A1) of SEQ ID NO: 6. An even more preferred embodiment, relates to a chimeric VLP formed by the fusion protein whose amino acid sequence is SEQ ID NO: 7.

Another preferred embodiment of this first aspect of the invention, relates to a chimeric VLP formed by a fusion protein comprising SEQ ID NO: 4 and SEQ ID NO: 6, wherein SEQ ID NO: 6 is inserted in SEQ ID NO: 4. As a result of the insertion of SEQ ID NO: 6, SEQ ID NO: 4 is divided into two parts. A more preferred embodiment, relates to a chimeric VLP formed by a fusion protein comprising SEQ ID NO: 4 and SEQ ID NO: 6, wherein SEQ ID NO: 6 is inserted in SEQ ID NO: 4, and additionally comprising one or two linker polypeptides of up to 15 amino acids each one situated between the amino acid sequence of SEQ ID NO: 6 and the amino acid sequences of the two parts into which SEQ ID NO: 4 is divided as a result of the insertion.

A preferred embodiment of this first aspect of the invention, relates to a chimeric VLP formed by a fusion protein comprising SEQ ID NO: 4 and SEQ ID NO: 6, wherein SEQ ID NO: 6 is inserted between the Leucine of position 436 ($L_{436}$) and the Lysine of position 437 ($K_{437}$) of SEQ ID NO: 4. A more preferred embodiment, relates to a chimeric VLP formed by a fusion protein comprising SEQ ID NO: 4 and SEQ ID NO: 6, wherein SEQ ID NO: 6 is inserted between amino acids $L_{436}$ and $K_{437}$ of SEQ ID NO: 4, and additionally comprising one or two linker polypeptides of up to 15 amino acids each one situated between the amino acid sequence of SEQ ID NO: 6 and the amino acid sequences of the two parts into which SEQ ID NO: 4 is divided as a result of the insertion. An even more preferred embodiment of this first aspect of the invention, relates to a chimeric VLP formed by a fusion protein whose amino acid sequence is SEQ ID NO: 8.

A preferred embodiment, relates to a chimeric VLP formed by a fusion protein comprising SEQ ID NO: 4 and SEQ ID NO: 6, wherein SEQ ID NO: 6 is inserted between the Alanine of position 441 ($A_{441}$) and the Phenylalanine of position 442 ($F_{442}$) of SEQ ID NO: 4. A more preferred embodiment, relates to a chimeric VLP formed by a fusion protein comprising SEQ ID NO: 4 and SEQ ID NO: 6, wherein SEQ ID NO: 6 is inserted between amino acids $A_{441}$ and $F_{442}$ of SEQ ID NO: 4, and additionally comprising one or two linker polypeptides of up to 15 amino acids each one situated between the amino acid sequence of SEQ ID NO: 6 and the amino acid sequences of the two parts into which SEQ ID NO: 4 is divided as a result of the insertion. An even more preferred embodiment of this first aspect of the invention, relates to a chimeric VLP formed by a fusion protein whose amino acid sequence is SEQ ID NO: 9.

A preferred embodiment, relates to a chimeric VLP formed by a fusion protein comprising SEQ ID NO: 4 and SEQ ID NO: 6, wherein SEQ ID NO: 6 is inserted between the Alanine of position 450 ($A_{450}$) and the Isoleucine of position 451 ($I_{451}$) of SEQ ID NO: 4. A more preferred embodiment, relates to a chimeric VLP formed by a fusion protein comprising SEQ ID NO: 4 and SEQ ID NO: 6, wherein SEQ ID NO: 6 is inserted between amino acids $A_{450}$ and $I_{451}$ of SEQ ID NO: 4, and additionally comprising one or two linker polypeptides of up to 15 amino acids each one situated between the amino acid sequence of SEQ ID NO: 6 and the amino acid sequences of the two parts into which SEQ ID NO: 4 is divided as a result of the insertion. An even more preferred embodiment of this first aspect of the invention, relates to a chimeric VLP formed by a fusion protein whose amino acid sequence is SEQ ID NO: 10.

A second aspect of the invention relates to a process for obtaining the chimeric VLP of the invention, which comprises cultivating a host cell that comprises a nucleic acid encoding the fusion protein of the invention, under conditions that allow the expression of said fusion proteins, and the assembly of said fusion proteins to form chimeric VLP.

A preferred embodiment of this second aspect of the invention, relates to a process for obtaining the chimeric VLP particles of the invention, which comprises cultivating a host cell that comprises a nucleic acid encoding the fusion protein of the invention, under conditions that allow the expression of said fusion proteins, and the assembly of said fusion proteins to form chimeric VLP, and which additionally comprises isolating or purifying said chimeric VLP.

The fusion protein of the invention may be obtained by means of recombinant or genetic engineering techniques well known in the state of the art. The sequence of a nucleic acid that encodes the fusion protein of the invention (hereinafter, nucleic acid of the invention) may be obtained by means of any synthetic or biological method, for example, but without limitation, the restriction of suitable sequences or the amplification of the DNA sequence of the protein of interest through polymerase chain reaction (PCR).

The nucleic acid may be comprised in a gene construct (hereinafter gene construct of the invention). This gene construct of the invention may comprise the nucleic acid of the invention, operatively linked to a sequence regulating the expression of the nucleic acid of the invention, thereby constituting an expression cassette.

"Operatively linked" refers to a juxtaposition wherein the components thus described have a relationship that allows them to function in the intended manner. A control sequence "operatively linked" to the nucleic acid, is linked thereto in such a way that the expression of the sequence encoding the nucleic acid is achieved.

"Control sequence" refers to sequences of nucleic acids that affect the expression of the sequences whereto they are linked. Said control sequences include, for example, but without limitation, promoters, initiation signals, termination signals, intensifiers or silencers. The term "control sequences" is intended to include those components whose presence is necessary for the expression, and may also include additional components whose presence is advantageous.

In a preferred embodiment, the gene construct of the invention comprises the nucleic acid of the invention operatively linked to, at least, one control sequence of the list that comprises:

a. a promoter, b. a transcription initiation signal, c. a transcription termination signal, d. a polyadenylation signal, or e. a transcriptional activator.

As used herein, the term "promoter" refers to a region of DNA situated in position 5' in respect of the transcription initiation point and that is necessary or facilitates said transcription in an animal cell. This term includes, for example, but without limitation, constituent promoters, specific promoters of the cell type or of tissue or inducible or repressible promoters.

The control sequences depend on the origin of the cell wherein the nucleic acid of the invention is to be expressed. In a particular embodiment, the expression control sequences linked to the nucleic acid of the invention are functional in prokaryote organisms and cells, for example, but without limitation, bacteria; whereas in another particular embodiment, said expression control sequences are functional in eukaryote organisms and cells, for example, yeast cells or animal cells.

The nucleic acid of the invention or gene construct of the invention may be introduced inside a cell, referred to as a host cell, for example, but without limitation, in the form of a naked nucleic acid or by means of a vector.

The term "cloning vector", as used in the present description, refers to a molecule of DNA wherein another fragment of DNA may be integrated, without it losing the capacity to self-replicate. Examples of expression vectors are, but without limitation, plasmids, cosmids, DNA phages or artificial yeast chromosomes.

The term "expression vector", as used in the present description, refers to a cloning vector suitable for expressing a nucleic acid that has been cloned therein after being introduced in a cell, referred to as the host cell. Said nucleic acid is, in general, operatively linked to control sequences.

The term "host cell", as used in the present description, refers to any prokaryote or eukaryote organism that is the receiver of an expression vector, cloning vector or any other DNA molecule.

A third aspect of the invention relates to the use of the chimeric VLP of the invention in the production of a drug, preferably, a vaccine.

A fourth aspect of the invention relates to the use of the chimeric VLP of the invention in the production of a drug for the prevention and/or treatment of an infection caused by HPV, preferably, HPV-16.

A fifth aspect of the invention relates to the use of the chimeric VLP of the invention in the production of a drug for the prevention and/or treatment of a neoplasia caused by the human papillomavirus.

A sixth aspect of the invention relates to a pharmaceutical composition (hereinafter, pharmaceutical composition of the invention) comprising the chimeric VLP of the invention.

A preferred embodiment of this sixth aspect of the invention relates to a pharmaceutical composition comprising the chimeric VLP of the invention and additionally comprising a pharmaceutically acceptable vehicle. Another preferred embodiment of this sixth aspect of the invention relates to a pharmaceutical composition comprising the chimeric VLP of the invention and additionally comprising another active principle. A more preferred embodiment of this sixth aspect of the invention relates to a pharmaceutical composition comprising the chimeric VLP of the invention, a pharmaceutically acceptable vehicle and additionally another active principle.

As used herein, the terms "active principle", "active substance", "pharmaceutically active substance", "active ingredient", or "pharmaceutically active ingredient" refer to any component which potentially provides pharmacological activity or other different effect on the diagnosis, cure, mitigation, treatment or prevention of a disease, or which affects the structure or function of the body of humans or other animals.

The pharmaceutical composition of the invention may be formulated for administration through a variety of forms known in the state of the art. Such formulations may be administered to an animal, and more preferably, to a mammal, including a human being, through a variety of routes, including, but without limitation, parenteral, intraperitoneal, intravenous, intradermal, epidural, intraspinal, intrastromal, intraarticular, intrasynovial, intrathecal, intralesional, intraarterial, intracapsular, intracardiac, intramuscular, intranasal, intracraneal, subcutaneous, intraorbital, intracapsular or topical.

The dose for obtaining a therapeutically effective amount will depend on a variety of factors, such as, for example, age, weight, sex or tolerance of the animal. In the sense used in this description, the expression "therapeutically effective amount" refers to the amount of the pharmaceutically effective composition that produces the required effect and, in general, will be determined, among other causes, by the characteristics inherent to the pharmaceutical composition in question and the therapeutic effect to be achieved. The pharmaceutically acceptable "adjuvants" or "vehicles" that may be used in such composition are the vehicles known in the state of the art.

Throughout the description and the claims the word "comprises" and its variants are not intended to exclude other technical characteristics, additives, components or steps. For persons skilled in the art, other objects, advantages and characteristics of the invention will be inferred in part from the description and in part from the practice of the invention. The following figures and examples are provided by way of illustration, and are not intended to limit the present invention.

EXAMPLES

Figure 1:
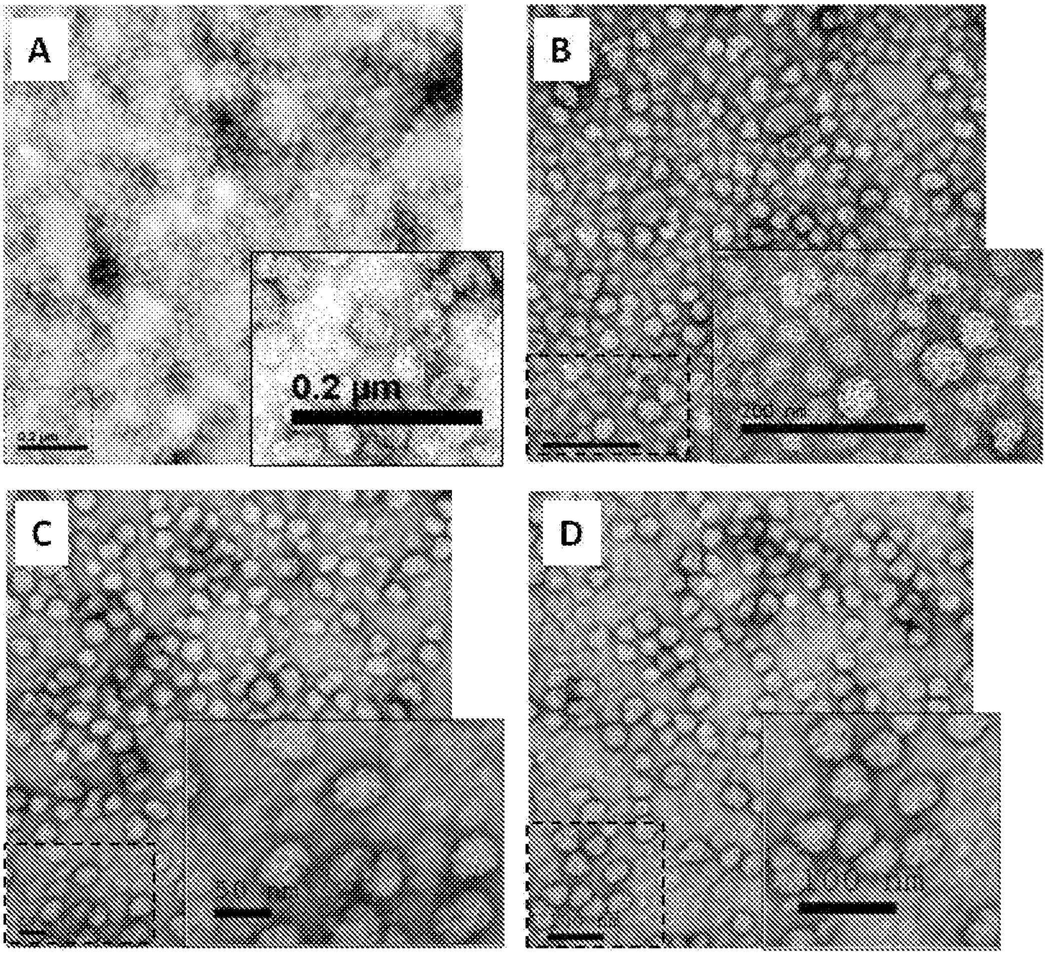
FIG. 1. Shows the microphotographs by scanning electron microscope of the virus-like particles resulting from the expression fusion proteins a) $VP2_{452}$-$E7_{\Delta 1\text{-}44}$; b) $VP2_{452}(L_{436}\uparrow E7_{\Delta 1\text{-}44}\uparrow K_{437})$; c) $VP2_{452}(A_{441}\uparrow E7_{\Delta 1\text{-}44}\uparrow F_{442})$; d) $VP2_{452}(A_{450}\uparrow E7_{\Delta 1\text{-}44}\uparrow I_{451})$. The dotted line in each photograph (left, bottom) corresponds to the amplified part. The scale bars appear on each photograph.
Figure 2:
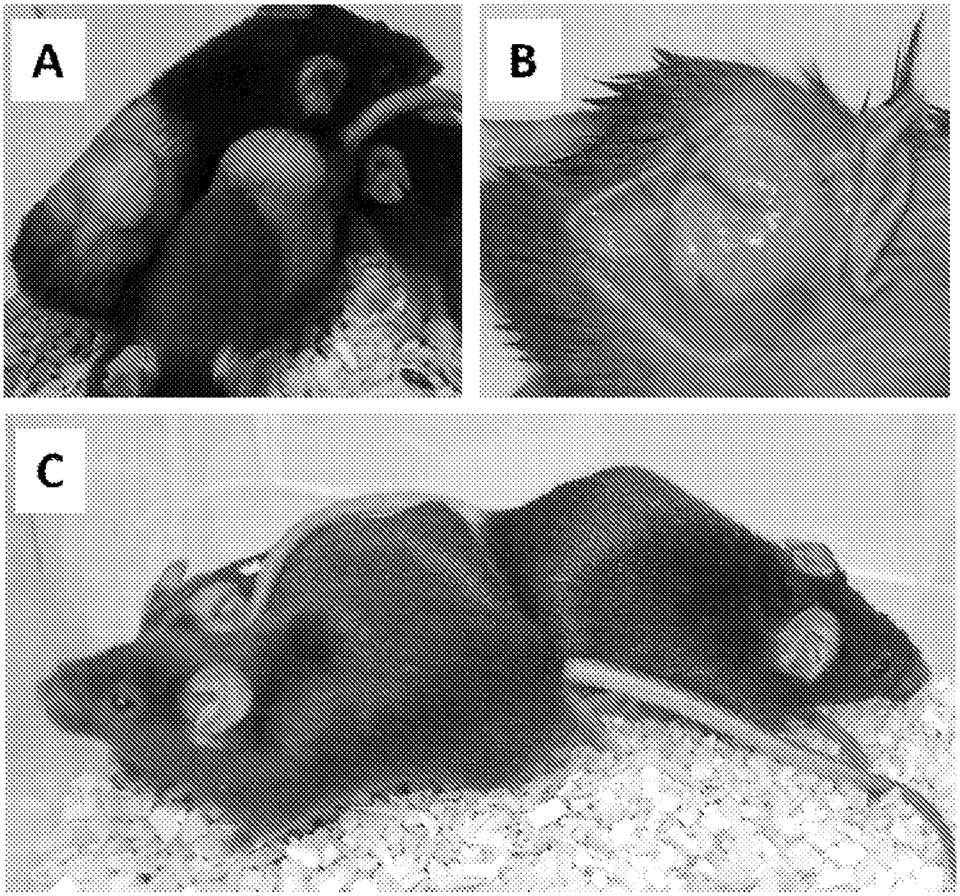
FIG. 2. C57BL/6-TgN(HLA-A2.1) mice after 25 days of being xenotransplanted subcutaneously with TC1/A2 cells: (A) mice vaccine with control VLP ($VP2_{452}$) showing tumours of approximately 1 $cm^3$; (B) necropsy of mouse vaccinated with control VLP ($VP2_{452}$); (C) representative photo of mice vaccinated with VLP containing sequences of E7 and that are tumour-free.

The following specific examples provided in this patent document serve to illustrate the nature of the present invention. These examples are included for solely illustrative purposes and are not to be interpreted as limitations of the invention claimed herein. Therefore, the examples described below illustrate the invention without limiting the field of application thereof.

Example 1

Search and Selection, by Means of a Successive Screening Process, of Chimeric VLP Based on Carboxyl-Terminals Fusions of VP2 with E7 Sequences of HPV With a view to identifying chimeric virus-like particles effective in the treatment of neoplasias caused by HPV different constructs are generated incorporating the VP2 protein truncated in different points of its carboxyl terminal and different E7 sequences of HPV. To this effect, DNA constructs are produced in the expression plasmid pESC-URA (Stratagene™) which express VP2 truncated in their carboxyl end in the amino acids in position 452, 450, 449, 446, 443, 441 ($VP2_{452}$, $VP2_{450}$, $VP2_{449}$, $VP2_{446}$, $VP2_{443}$, $VP2_{441}$), and incorporating restriction sites NotI and HindIII in the carboxyl terminal end pESC-URA/$VP2_{452}$ NotI-HindIII; pESC-URA/$VP2_{450}$ NotI-HindIII; pESC-URA/$VP2_{449}$ NotI-HindIII; pESC-URA/$VP2_{446}$ NotI-HindIII; pESC-URA/$VP2_{443}$ NotI-HindIII; and pESC-URA/$VP2_{441}$ NotI-HindIII. Following the NotI-HindIII double digestion in the carboxyl terminal of the different VP2 a sequence is cloned expressing the E7 protein of HPV-16 wherein the amino acid sequences 1 to 35 ($E7\Delta_{1\text{-}35}$) associated to its oncogenicity have been eliminated. As shown in Table 1, the capacity to produce VLP in *Saccharomyces cerevisiae* Y449 transformed with the different resulting expression vectors, pESC-URA/$VP2_{452}$-$E7\Delta_{1\text{-}35}$ to express fusion protein $VP2_{452}$-$E7\Delta_{1\text{-}35}$ [SEQ ID NO: 5], pESC-URA/$VP2_{450}$-$E7\Delta_{1\text{-}35}$ to express fusion protein $VP2_{450}$-$E7\Delta_{1\text{-}35}$ [SEQ ID NO: 11], pESC-URA/$VP2_{449}$-$E7\Delta_{1\text{-}35}$ to express fusion protein $VP2_{449}$-$E7\Delta_{1\text{-}35}$ [SEQ ID NO: 12], pESC-URA/$VP2_{446}$-$E7\Delta_{1\text{-}35}$ to express fusion protein $VP2_{446}$-$E7\Delta_{1\text{-}35}$ [SEQ ID NO: 13], pESC-URA/$VP2_{443}$-$E7\Delta_{1\text{-}35}$ to express fusion protein $VP2_{443}$-$E7\Delta_{1\text{-}35}$ [SEQ ID NO: 14], pESC-URA/$VP2_{441}$-$E7\Delta_{1\text{-}35}$ to express fusion protein $VP2_{441}$-$E7\Delta_{1\text{-}35}$ [SEQ ID NO: 15], is compared to that of pESC-URA/$VP2_{452}$ to express protein $VP2_{452}$ [SEQ ID NO: 4]. As part of the same experiment fusions are also generated to the carboxyl terminal of $VP2_{452}$ based on the double digestion NotI-HindIII of pESC-URA/$VP2_{452}$ NotI-HindIII and cloning of different sequences expressing the E7 protein of HPV-16 wherein amino acids 1-40 ($E7_{\Delta 1\text{-}40}$) have been eliminated to express the fusion protein $VP2_{452}$-$E7\Delta_{1\text{-}40}$ [SEQ ID NO: 16], amino acids 1-41 (HPV16 $E7_{\Delta 1\text{-}41}$) to express the fusion protein $VP2_{452}$-$E7\Delta_{1\text{-}41}$ [SEQ ID NO: 17], and amino acids 1-44 (HPV16 $E7_{\Delta 1\text{-}44}$) to express the fusion protein $VP2_{452}$-$E7\Delta_{1\text{-}44}$ [SEQ ID NO: 7]. As shown in Table 1, the capacity to produce VLP in *S. cerevisiae* Y449 transformed with the different resulting expression vectors, pESC-URA/$VP2_{452}$-$E7_{\Delta 1\text{-}40}$, pESC-URA/$VP2_{452}$-$E7_{\Delta 1\text{-}41}$ or pESC-URA/$VP2_{452}$-$E7_{\Delta 1\text{-}44}$ is compared to that of pESC-URA/$VP2_{452}$ NotI-HindIII. The capacity of the different constructs to produce VLP is determined by means of a conformational antibody that recognises the three-dimensional structure of the VLP and subsequently analysed by means of an ELISA-type immunoassay. At the same time, the production and purification of the chimeric VLP and control VLP for morphological studies and in vivo tests is carried out following a standard process for yeast culture during 48 hours, concentration through centrifugation, mechanical lysing, precipitation in ammonium sulphate, purification by means of gel filtration chromatography. In all cases, the presence of VLP is confirmed by electron microscope and the chimeric VLP produced are quantified through protein electrophoresis in polyacrylamide gel under denaturing conditions.

The performance in the production of the chimeric VLP evaluated is set out in Table 1. As the next step in the selection process, the capacity to induce an immune response is evaluated of the VLP resulting from the expression of the constructs with VLP production efficiency comparable or superior to the control $VP2_{452}$-$E7_{\Delta 1\text{-}35}$. In summary, the ELISPOT assay is aimed at measuring the induction of response in cytotoxic T lymphocytes (CTL) in a mouse model. To this effect transgenic C57BL/6-TgN(HLA-A2.1)1Enge/J mice are used, humanized with the histocompatibility complex HLA-A2. The mice are inoculated in groups of eight by means of subcutaneous administration of the chimeric VLP on days 0 and 14. On day 20 the animals are sacrificed, spleens are removed and splenocytes are isolated. Once isolated, the splenocytes are cultivated in the presence of IL-2 and subsequently stimulated with specific peptides (T epitopes) of protein E7 of HPV-16 during 24 hours. Following incubation, the expression of IFN-γ of the clones of CTLs is evaluated as a measurement of their activation. The capacity to induce a specific CTL response against T epitopes of protein E7 of HPV-16 of each one of the evaluated chimeric VLP is set out in Table 1 wherein the number of "+" represents the intensity of the induced response.

As a final step in the selection process, the antitumoral activity of the chimeric VLP with the highest values of performance in VLP production and the best results in the ELISPOT assay is evaluated. To evaluate the antitumoral activity a cell and animal model of tumour induction is used wherein $5\times10^5$ cells TC1/A2 [according to Peng S. et al. Gene Therapy, 13:257-265 (2006)] over-expressing tumoral antigens E6 and E7 of HPV-16 are implanted subcutaneously in C57BL/6-TgN(HLA-A2.1)1Enge/J mice humanized with the histocompatibility complex HLA-A2. The animals are divided into groups of ten and each animal is administered 50 ug of the chimeric or control VLP through subcutaneous administration on days 5 and 12 after induction of the tumour. Periodically, tumour development is determined and the weight of the animals is monitored. The animals with tumours having a volume in excess of 1 $cm^3$ are sacrificed. The therapeutic effect of the chimeric VLP on tumour model TC1/A2 is set out in Table 1 which shows the percentage of animals that survived 60 days after induction of the tumour.

As a final result of this process, the chimeric VLP is selected containing construct $VP2_{452}$-$E7_{\Delta1\text{-}44}$, wherein the sequence of truncated E7 $E7_{\Delta1\text{-}44}$ is fused to the carboxyl terminal end of VP2 in the Arginine (R) of position 452.

TABLE 1

| Clone | Identification | % VLP | ELISPOT | Antitumoral effect Survival % |
|---|---|---|---|---|
| 1 | $VP2_{452}$-$E7_{\Delta1\text{-}35}$ | 20% | +++ | 80% |
| 2 | $VP2_{450}$-$E7_{\Delta1\text{-}35}$ | 16% | ND | ND |
| 3 | $VP2_{449}$-$E7_{\Delta1\text{-}35}$ | 20% | +++ | ND |
| 4 | $VP2_{446}$-$E7_{\Delta1\text{-}35}$ | 14% | ND | ND |
| 5 | $VP2_{443}$-$E7_{\Delta1\text{-}35}$ | 8% | ND | ND |
| 6 | $VP2_{441}$-$E7_{\Delta1\text{-}35}$ | 16% | ++ | ND |
| 7 | $VP2_{452}$-$E7_{\Delta1\text{-}40}$ | 25% | +++ | ND |
| 8 | $VP2_{452}$-$E7_{\Delta1\text{-}41}$ | 25% | +++ | ND |
| 9 | $VP2_{452}$-$E7_{\Delta1\text{-}44}$ | 40% | ++++ | 100% |
| 10 | $VP2_{452}$ | 100% | – | 0% |

% VLP: Performance in the production of VLP compared to $VP2_{452}$;
ND: Not determined.

Example 2

Cloning, Search and Selection, by Means of a Successive Screening Process, of Chimeric VLP with Therapeutic Efficacy Against Neoplasias Caused by the Human Papillomavirus In a first step, the process is carried out of random insertion in the VP2 gene of the sequences encoding non-transforming regions of E7 wherein amino acids 1 to 44 ($E7_{\Delta1\text{-}44}$) have been deleted. For this a library is prepared of VP2 truncated in the carboxyl end as of amino acid 452 ($VP2_{452}$), which contains random insertions of transposon Mu throughout its sequence. In a next step, the insert of transposon Mu is replaced by an insert [SEQ ID NO: 18] containing the kanamycin resistance gene and unique restriction sites NotI and SpeI at its ends. The cloned insert facilitates the incorporation of inserts $E7_{\Delta1\text{-}44}$ [SEQ ID NO: 19] or $E7_{\Delta1\text{-}44}$(linker) [SEQ ID NO: 20] of HPV-16 synthesized to contain ends Bsp120I (compatible with NotI) and SpeI for cloning in each one of the three possible reading frames. The fusion of inserts $E7_{\Delta1\text{-}44}$ or $E7_{\Delta1\text{-}44}$(linker) generates additional amino acids at the point of fusion between $VP2_{452}$ and $E7_{\Delta1\text{-}44}$. The insert $E7_{\Delta1\text{-}44}$ (linker) additionally contains sequences GGGGS [SEQ ID NO: 21] at the two ends of $E7_{\Delta1\text{-}44}$ that have been introduced in order to increase the flexibility of insertion ("linkers").

Following the double digestion of the library with NotI and SpeI and the link in the presence of the fragments with ends Bsp 120I and SpeI of $E7_{\Delta1\text{-}44}$ or $E7_{\Delta1\text{-}44}$(linker), electro-competent cells of *E. coli* are transformed in order 4 to obtain a library of $VP2_{452}$ containing random insertions of $E7_{\Delta1\text{-}44}$. The library is expanded and 10 ug of the DNA obtained from it is used to transform *S. cerevisiae* Y449 which is then seeded on Petri dishes containing the medium YNB/CSM-URA with 2% glucose. The approximately 10,000 clones obtained are transferred to selection Petri dishes containing galactose. The colonies obtained from the selection are transferred to PVDF membranes for colony immunoblot identification of those that express VP2 and E7.

In a second step, a selection process is carried out of the recombinant yeast clones whose performance in VLP production is effective and which contain $E7_{\Delta1\text{-}44}$. To this effect, cultures are prepared in conditions of expression of fifty clones with the highest signals in the colony immunoblot against VP2 and E7 and after 48 hours of incubation protein extracts are prepared wherein the amount of VLP is quantified by means of an ELISA-type assay that incorporates an antibody which specifically recognises the three-dimensional structure of the VLP formed by VP2. In this first screening, those constructs are selected with the highest performances in VLP production. The presence of the complete sequence of $E7_{\Delta1\text{-}44}$ and its place of insertion is verified through sequencing of a DNA extract of each one of the selected clones. As set out in Table 2, in this way 12 clones are identified expressing VLP of $VP2_{452}$ containing insert $E7_{\Delta1\text{-}44}$ and having a production performance compared with the control VLP of ($VP2_{452}$), of between 6 and 20%.

At the same time, the production and purification of the chimeric VLP and control VLP for morphological studies and for in vivo tests is carried out following a standard yeast culture process during 48 hours, concentration by means of centrifugation, mechanical lysing, precipitation in ammonium sulphate, purification by means of gel filtration chromatography. In all cases the presence of VLP is confirmed through electron microscopy and the chimeric VLP produced are quantified by means of protein electrophoresis in polyacrylamide gel under denaturing conditions.

In a third step, the chimeric VLP that generate a significant immune response against E7 are selected. For this purpose, the capacity to induce an immune response of the chimeric VLP originated by those constructs having the highest production performance is evaluated. In summary, the ELISPOT assay is aimed at measuring the induction of a cytotoxic T lymphocyte (CTL) response in a mouse model. To this effect, transgenic C57BL/6-TgN(HLA-A2.1)1Enge/J mice are used "humanized" with histocompatibility complex HLA-A2. The mice are inoculated in groups of eight by subcutaneous administration of the chimeric VLP on days 0 and 14. On day 20 the animals are sacrificed, spleens are extracted and splenocytes isolated. Once isolated, the splenocytes are cultivated in the presence of IL-2 and subsequently stimulated with specific peptides (T epitopes) of protein E7 of HPV-16 during 24 hours. Following incubation, the expression of IFN-γ of the CTL clones is evaluated as a measurement of their activation. The capacity to induce a specific CTL response against the epitopes of protein E7 of HPV-16 of each one of the evaluated chimeric VLP is set out in Table 1 wherein the number of "+" represents the intensity of the induced response.

In a fourth step in the selection process, the antitumoral activity of the chimeric VLP having the highest VLP production performances and the best results in the ELISPOT assay is evaluated. For the evaluation of the antitumoral activity a cell and animal model of tumour induction is used wherein $5\times10^5$ cells TC1/A2 [according to Peng S. et al. Gene Therapy, 13:257-265 (2006)] over-expressing tumoral antigens E6 and E7 of HPV-16, are implanted subcutaneously in C57BL/6-TgN(HLA-A2.1)1Enge/J mice humanized with histocompatibility complex HLA-A2. The animals are divided into groups of eight and each animal is administered 50 ug of the chimeric or control VLP, via subcutaneous administration on days 5 and 12 after tumour induction. Periodically, tumour development is determined and the weight of the animals is monitored. Animals with tumours of a volume higher than 1 $cm^3$ are sacrificed. The therapeutic effect of the chimeric VLP on tumour model TC1/A2 is set out in Table 2 which shows the percentage of animals that survived 60 days after tumour induction.

As the final result of this process, three chimeric VLP object of the present invention are selected, in other words:

a) $VP2_{452}(L_{436}\uparrow E7_{\Delta1\text{-}44}\uparrow K_{437})$ [SEQ ID NO: 8]: chimeric VLP wherein the $E7_{\Delta1\text{-}44}$ sequence is inserted between the Leucine in position 436 and the Lysine in position 437 of the VP2 of 452 amino acids in length;

b) $VP2_{452}(A_{441}\uparrow E7_{\Delta1\text{-}44}\uparrow F_{442})$ [SEQ ID NO: 9]: chimeric VLP wherein the $E7_{\Delta1\text{-}44}$ sequence is inserted between the Alanine in position 441 and the Phenylalanine in position 442 of the VP2 of 452 amino acids in length; and c) $VP2_{452}(A_{450}\uparrow E7_{\Delta1\text{-}44}\uparrow I_{451})$ [SEQ ID NO: 10]: chimeric VLP wherein the $E7_{\Delta1\text{-}44}$ sequence is inserted between the Alanine in position 450 and the Isoleucine in position 451 of the VP2 of 452 amino acids in length.

TABLE 2

| | Clone Identification | % VLP | ELISPOT Result | Antitumoral effect Survival % |
|---|---|---|---|---|
| 1 | $VP2_{452}(Q_{10}\uparrow E7_{\Delta1\text{-}44}\uparrow I_{11})$ | 10% | +++ | 60% |
| 2 | $VP2_{452}(D_{51}\uparrow E7_{\Delta1\text{-}44}\uparrow T_{52})$ | 6% | ND | ND |
| 3 | $VP2_{452}(T_{73}\uparrow E7_{\Delta1\text{-}44}\uparrow L_{74})$ | 6% | ND | ND |
| 4 | $VP2_{452}(A_{380}\uparrow E7_{\Delta1\text{-}44}\uparrow K_{380})$ | 8% | ND | ND |
| 5 | $VP2_{452}(L_{436}\uparrow E7_{\Delta1\text{-}44}\uparrow K_{437})$ | 10% | +++++ | 100% |
| 6 | $VP2_{452}(A_{441}\uparrow E7_{\Delta1\text{-}44}\uparrow F_{442})$ | 20% | +++++ | 100% |
| 7 | $VP2_{452}(A_{450}\uparrow E7_{\Delta1\text{-}44}\uparrow I_{451})$ | 18% | +++++ | 100% |
| 8 | $VP2_{452}\text{-}E7_{\Delta1\text{-}44}$ | 40% | +++++ | 100% |
| 9 | $VP2_{452}$ | 100% | – | 0% |

% VLP: Performance in VLP production compared with $VP2_{452}$;
ND: Not determined.

The invention claimed is:

1. A chimeric virus-like particle (VLP) formed by a fusion protein consisting of:

a subunit (a) consisting of a pVP2 protein of Birnavirus or a fragment thereof selected from the group consisting of $VP2_{441}$, $VP2_{443}$, $VP2_{446}$, $VP2_{449}$, $VP2_{450}$, and $VP2_{452}$, and a subunit (b) consisting of SEQ ID NO: 6.

2. The chimeric virus-like particle according to claim 1, wherein subunit (a) is SEQ ID NO: 4, $VP2_{441}$, $VP2_{443}$, $VP2_{446}$, $VP2_{449}$ or $VP2_{450}$.

3. The chimeric virus-like particle according to claim 1, wherein subunit (b) is linked to the carboxyl-terminal end of subunit (a).

4. A chimeric virus-like particle formed by a fusion protein consisting of:

a subunit (a) consisting of the pVP2 protein of Birnavirus or a fragment thereof selected from the group consisting of $VP2_{441}$, $VP2_{443}$, $VP2_{446}$, $VP2_{449}$, $VP2_{450}$, and $VP2_{452}$, a subunit (b) consisting of SEQ ID NO: 6, and a linker peptide of up to 10 amino acids, wherein subunit (b) is linked to the carboxyl-terminal end of subunit (a) by the linker peptide situated between the amino acid sequences of subunits (a) and (b).

5. The chimeric virus-like particle according to claim 3, wherein subunit (b) is SEQ ID NO: 6 and is linked to $R_{452}$ of subunit (a) which is SEQ ID NO: 4.

6. The chimeric virus-like particle according to claim 1, wherein the fusion protein has an amino acid sequence as set forth in SEQ ID NO: 7.

7. The chimeric virus-like particle according to claim 1, wherein subunit (b) is inserted in subunit (a) at a location between amino acids $L_{436}$ and $K_{437}$, between amino acids $A_{441}$ and $F_{442}$, or between amino acids $A_{450}$ and $I_{451}$ of subunit (a) wherein amino acids $L_{436}$, $K_{437}$, $A_{441}$, $F_{442}$, $A_{450}$ and $I_{451}$ correspond to the positions of SEQ ID NO: 4.

8. A chimeric virus-like particle formed by a fusion protein consisting of:

a subunit (a) consisting of the pVP2 protein of Birnavirus or a fragment thereof selected from the group consisting of $VP2_{441}$, $VP2_{443}$, $VP2_{446}$, $VP2_{449}$, $VP2_{450}$, and $VP2_{452}$, a subunit (b) consisting of SEQ ID NO: 6, and one or two linker peptides of up to 15 amino acids, wherein subunit (b) is inserted in subunit (a) at a location between amino acids $L_{436}$ and $K_{437}$, between amino acids $A_{441}$ and $F_{442}$, or between amino acids $A_{450}$ and $I_{451}$ of subunit (a) wherein amino acids $L_{436}$, $K_{437}$, $A_{441}$, $F_{442}$, $A_{450}$ and $I_{451}$ correspond to the positions of SEQ ID NO: 4, and the one or two linker peptides are situated between the amino acid sequence of subunit (b) and the amino acid sequence of subunit (a).

9. The chimeric virus-like particle according to claim 7, wherein subunit (b) is SEQ ID NO: 6 and is inserted between amino acids $L_{436}$ and $K_{437}$ of subunit (a) which is SEQ ID NO: 4.

10. The chimeric virus-like particle according to claim 7, wherein fusion protein has an amino acid sequence as set forth in SEQ ID NO: 8.

11. The chimeric virus-like particle according to claim 7, wherein subunit (b) is SEQ ID NO: 6 and is inserted between amino acids $A_{441}$ and $F_{442}$ of subunit (a) wherein amino acids $A_{441}$ and $F_{442}$ correspond to the positions of SEQ ID No: 4.

12. The chimeric virus-like particle according to claim 11, wherein the fusion protein has an amino acid sequence as set forth in SEQ ID NO: 9.

13. The chimeric virus-like particle according to claim 7, wherein subunit (b) is SEQ ID NO: 6 and is inserted between amino acids $A_{450}$ and $I_{451}$ of subunit (a) wherein amino acids $A_{450}$ and $I_{451}$ correspond to the positions of SEQ ID No: 4.

14. The chimeric virus-like particle according to claim 13, wherein the fusion protein has an amino acid sequence as set forth in SEQ ID NO: 10.

15. A process for obtaining the chimeric virus-like particles according to claim 1, which comprises cultivating a host cell that comprises a nucleic acid encoding the fusion protein according to claim 1 under conditions that allow the expression of said fusion proteins, and the assembly of said fusion proteins in order to form chimeric virus-like particles.

16. The process for obtaining chimeric virus-like particles according to claim 15, which further comprises isolating or purifying said chimeric virus-like particles.

17. A method of treatment of a neoplasia caused by the human papillomavirus comprising administering to a patient in need thereof a composition that comprises the virus-like particle according to claim 1.

18. The method according to claim 17 wherein the neoplasia is cervical cancer.

19. A pharmaceutical composition comprising the chimeric virus-like particle according to claim 1.

20. The pharmaceutical composition according to claim 19 additionally comprising a pharmaceutically acceptable vehicle.

* * * * *